United States Patent
Fleming et al.

(10) Patent No.: US 9,119,618 B2
(45) Date of Patent: Sep. 1, 2015

(54) SURGICAL DRAPE

(71) Applicants: Michelle Fleming, Addison, TX (US); William R. Woods, Rockwall, TX (US)

(72) Inventors: Michelle Fleming, Addison, TX (US); William R. Woods, Rockwall, TX (US)

(73) Assignee: SPECTRUM LABORATORIES, INC., Rancho Dominguez, CA (US)

( * ) Notice: Subject to any disclaimer, the term of this patent is extended or adjusted under 35 U.S.C. 154(b) by 250 days.

(21) Appl. No.: 13/792,917

(22) Filed: Mar. 11, 2013

(65) Prior Publication Data

US 2014/0251345 A1    Sep. 11, 2014

(51) Int. Cl.
*A61B 19/00* (2006.01)
*A61B 19/08* (2006.01)

(52) U.S. Cl.
CPC .............. *A61B 19/081* (2013.01); *A61B 19/08* (2013.01); *A61B 19/088* (2013.01)

(58) Field of Classification Search
CPC ................ A61B 19/2203; A61B 2017/00477; A61B 19/081; A61B 17/3423; A61B 2017/3445; A61B 2019/2215; A61B 2019/2223; A61B 2019/223; A61B 2019/448; A61B 19/08; A61B 2019/085; A61B 2019/086
USPC .................................................. 128/849–856
See application file for complete search history.

(56) References Cited

U.S. PATENT DOCUMENTS

| | | | | |
|---|---|---|---|---|
| 1,597,556 A | * | 8/1926 | Townsend | 604/357 |
| 3,386,444 A | * | 6/1968 | Brenner et al. | 604/357 |
| 4,105,019 A | * | 8/1978 | Haswell | 600/580 |
| 4,559,937 A | * | 12/1985 | Vinson | 604/356 |
| 4,570,628 A | * | 2/1986 | Neal | 128/853 |
| 5,002,069 A | * | 3/1991 | Thompson et al. | 128/849 |

* cited by examiner

*Primary Examiner* — Michael Brown
(74) *Attorney, Agent, or Firm* — Kenneth L. Green; Averill & Green

(57) ABSTRACT

A surgical drape includes two movable pockets allowing a smaller diameter and therefore saving space on an operating room table. A first smaller pocket extending from the drape is formed near the nose of the drape and includes an exit port for a lumen connected to a device inside the drape. A second larger pocket extending into the drape is formed behind the first pocket and allows a surgeon or technician to control or position the device without entering the interior of the drape or contacting the device.

13 Claims, 4 Drawing Sheets

SURGICAL DRAPE

The present invention relates to surgical drapes to cover devices used in used in operating rooms, and in particular to an improved surgical drape including pockets allowing a user to more easily manipulate the devices.

Preventing infections is a significant issue in hospitals. Surgical drapes are used in operating rooms to separate devices used during the surgery from open incisions to protect against infections.

One known surgical drape design is a wide drape, with edges sealed to allow the base to remain stationary, while devices are moved inside the drape. Unfortunately, this design requires excess material to allow the device to be able to move in the horizontal plane while the drape is stationary. This is a problem for the surgeon, because space in the operating suite is limited, and the extra material takes away from this valuable space in the operating suite. This design is also more cumbersome for the technician to use.

Another design covers devices with a disposable base unit, which is discarded when the surgery is complete. This design has two drawbacks. The first drawback is the extra expense for a single use device, and the disposal cost associated with it. The second drawback is having the drape positioned between the base and the device. This positioning allows potential for punching or tearing the drape during the operation, which could break the sterile barrier.

BRIEF SUMMARY OF THE INVENTION

The present invention addresses the above and other needs by providing a surgical drape which includes two movable pockets allowing a smaller diameter and therefore saving space on an operating room table. A first smaller pocket extending from the drape is formed near the nose of the drape and includes an exit port for a lumen connected to a device inside the drape. A second larger pocket extending into the drape is formed behind the first pocket and allows a surgeon or technician to control or position the device without entering the interior of the drape or contacting the device.

In accordance with one aspect of the invention, there is provided a method for using the surgical drape. The method includes: inserting a device into the surgical drape from an open tail end of the surgical drape; pushing the device to a location proximal to a closed nose end of the surgical drape; passing a lumen attached to the device through an exit port in a first small pocket of the surgical drape extending from the surgical drape near the nose end; placing a hand into a second larger pocket behind the first smaller pocket extending into the surgical drape; grasping the device with the hand, the surgical drape separating the hand from direct contact with the device; and moving the device without direct contact of the hand with the device.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figure 1A:
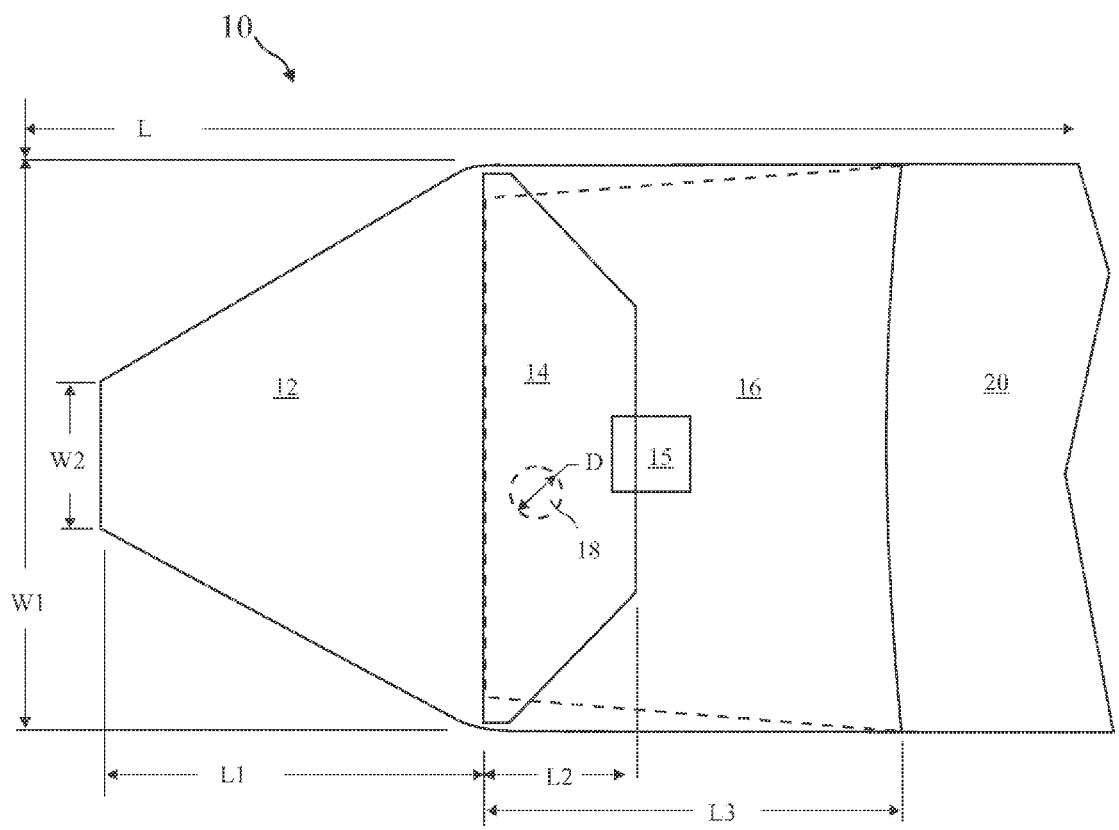
FIG. 1A is a top view of a surgical drape according to the present invention laying flat.
Figure 1B:
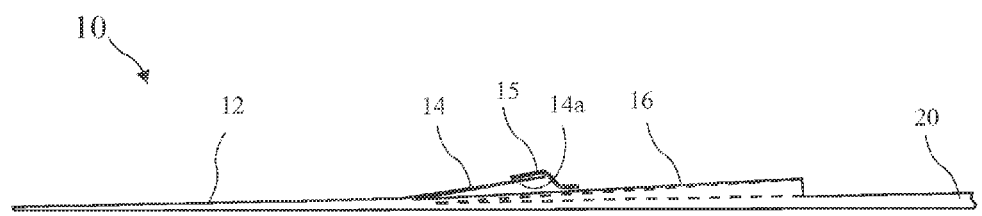
FIG. 1B is a side view of the surgical drape according to the present invention laying flat.

A top view of a surgical drape 10 according to the present invention is shown laying flat in FIG. 1A and a side view of the surgical drape 10 laying flat is shown in FIG. 1B. The surgical drape 10 includes a closed nose 12, a first smaller pocket 14 proximal to the nose 12, and second larger pocket 16 behind the smaller pocket 14, and a body 20. An exit port 18 is formed in one side of the smaller pocket 14, on a lower surface 14a of the smaller pocket 14 when the smaller pocket 14 is laying away from the nose 12. A small piece of tape 15 may be provided to hold the small pocket 14 against the surgical drape 10 (and in particular against a top surface of the large pocket 16) before use. The tape 15 is torn to release the small pocket 14.

The surgical drape 10 has a width W1 of between ten and twenty inches and preferably of about twelve inches and an overall length L of about eight feet when laying flat. The nose 12 tapers from the width W1 to a smaller width W2 of about three inches and has a length L1 of preferably between four and 20 inches and more preferably about eight inches. The smaller pocket 14 has a width about the same as the width w1 of the surgical drape 10 and a length L2 of preferably between two and twelve inches and more preferably about four inches when laying flat. The exit port 14 in the small pocket 14 has a diameter D of about one inch. The larger pocket 16 has a width about the same as the width W1 of the surgical drape and a length L3 of preferably between eight and twenty inches and more preferably about eight inches when laying flat.

Figure 2A:
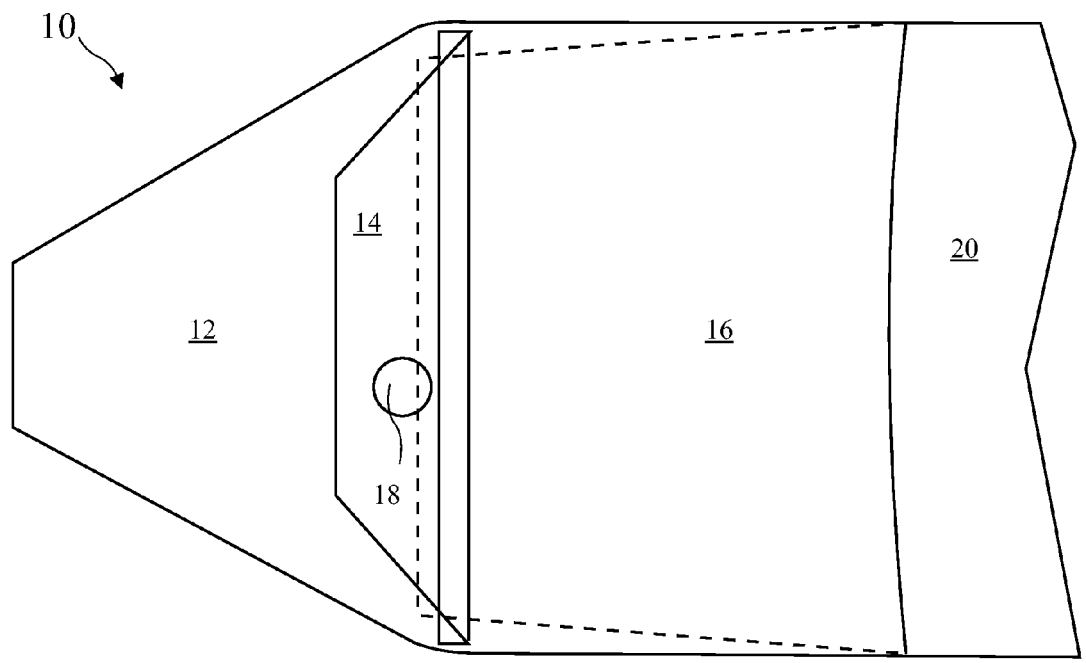
FIG. 2A is a top view of the surgical drape according to the present invention laying flat with a first smaller pocket folded forward.
Figure 2B:
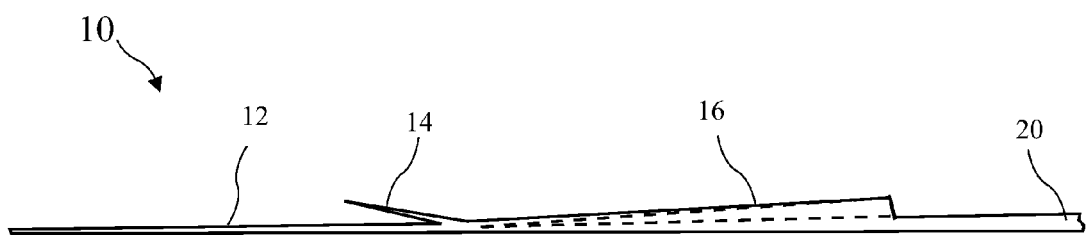
FIG. 2B is a side view of the surgical drape according to the present invention laying flat with the first smaller pocket laying forward.

A top view of the surgical drape 10 laying flat with the first smaller pocket 14 laying forward for use is shown in FIG. 2A, and a side view of the surgical drape 10 laying flat with the first smaller pocket 14 folded forward for use is shown in FIG. 2B. When the small pocket is folded forward, the exit port 18 is now exposed on a top surface of the small pocket 14.

Figure 3:
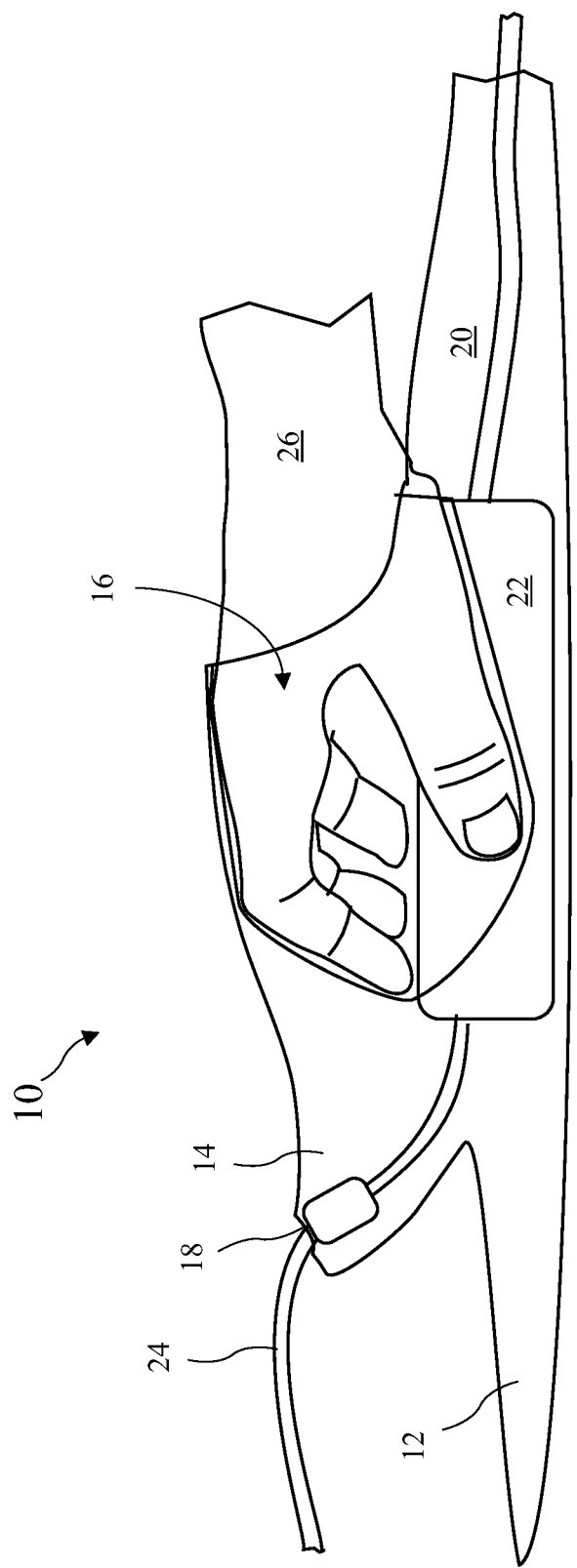
FIG. 3 is a side view of the surgical drape according to the present invention with a device residing in the surgical drape positioned by a user's hand.

A side view of the surgical drape 10 with a device 22 residing in the surgical drape positioned by a user's hand 26 is shown in FIG. 3. The device 22 includes a lumen 24 exiting the surgical drape 10 through the exit port 18. The hand 26 is able to position and reposition the device 22 without direct contact with the device 22 by reaching into the larger pocket 16.

Figure 4:
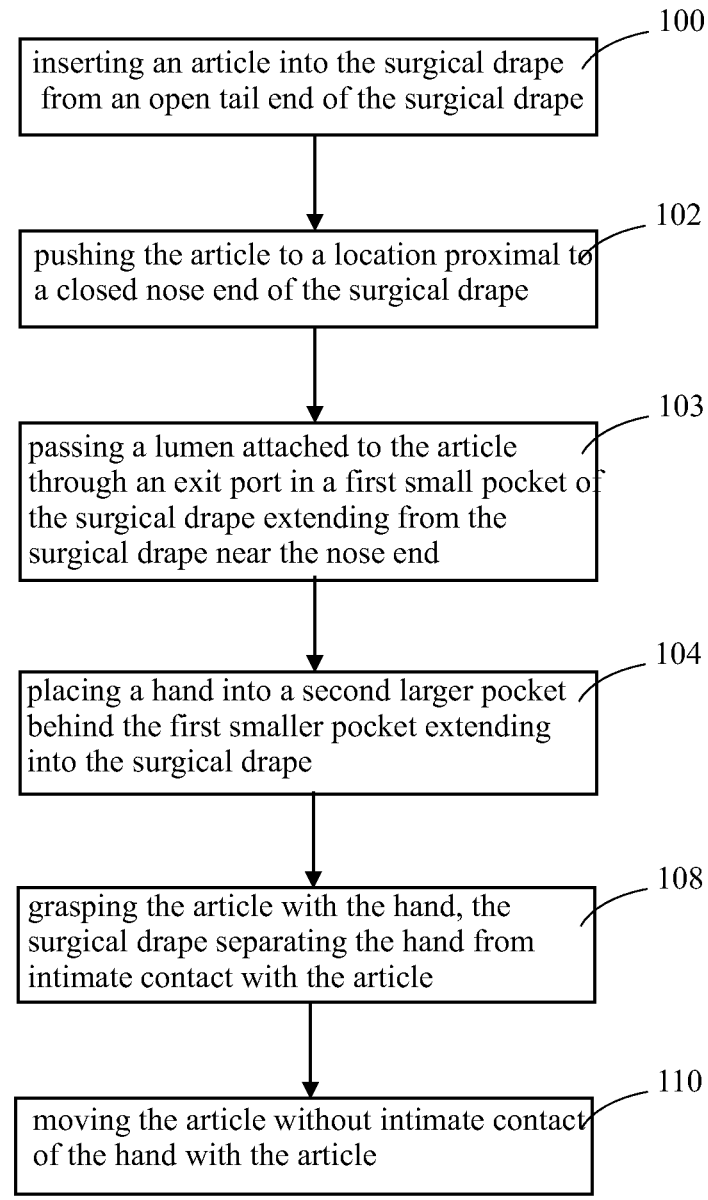
FIG. 4 is a method according to the present invention.

FIG. 4 is a method according to the present invention. The method includes inserting a device into the surgical drape from an open tail end of the surgical drape at step 100, pushing the device to a location proximal to a closed nose end of the surgical drape at step 102, passing a lumen attached to the device through an exit port in a first small pocket of the surgical drape extending from the surgical drape near the nose end at step 104, placing a hand into a second larger pocket behind the first smaller pocket extending into the surgical drape at step 106, grasping the device with the hand, the surgical drape separating the hand from direct contact with the device at step 108, and moving the device without direct contact of the hand with the device at step 110.

The surgical drape 12 is preferably made of plastic and more preferably made of clear plastic, and most preferably from polyethylene. The surgical drape 12 is preferably constructed by heat sealing seams.

While the invention herein disclosed has been described by means of specific embodiments and applications thereof, numerous modifications and variations could be made thereto by those skilled in the art without departing from the scope of the invention set forth in the claims.

We claim:

1. A surgical drape comprising:
    a long narrow body closed at a nose end, bottom, top, and sides, and open at a tail end forming a concave interior and flexible to allow insertion of a device through the open tail end into the interior of the long narrow body;
    a first smaller pocket extending upward in a convex manner from the top of the drape near the nose end, the smaller pocket open into the interior of the body;
    a small exit port in the smaller pocket providing a passage from the interior of the drape to an exterior of the drape; and
    a second larger pocket, larger than the smaller pocket, behind the first smaller pocket extending downward into the top of the surgical drape to form a concave opening in the top, the larger pocket flexible and wide enough to allow a hand to expand the pocket to allow the hand to reach into the interior of the drape and to grasp and manipulate the device.

2. The surgical drape of claim 1, wherein the surgical drape has a width W1 of about twelve inches when laying flat.

3. The surgical drape of claim 1, wherein the nose tapers from the width W1 to a smaller width W2 of about three inches.

4. The surgical drape of claim 3, wherein the nose has a length L1 of about six inches.

5. The surgical drape of claim 2 wherein the larger pocket has a width about the same as the width W1 of the surgical drape when laying flat.

6. The surgical drape of claim 5, wherein the larger pocket has a length L3 of about eight inches when laying flat.

7. The surgical drape of claim 2 wherein the smaller pocket has a width about the same as the width W1 of the surgical drape when laying flat.

8. The surgical drape of claim 7, wherein the smaller pocket has a length L2 of about three inches when laying flat.

9. The surgical drape of claim 1, wherein the exit port has a diameter D of about one inch.

10. The surgical drape of claim 1, wherein the surgical drape has an overall length L of about eight feet.

11. The surgical drape of claim 1, wherein the surgical drape is made of plastic.

12. The surgical drape of claim 11, wherein the surgical drape is made of clear plastic.

13. A method for using a surgical drape, the method comprising:
    inserting a device into the surgical drape from an open tail end of the surgical drape;
    pushing the device to a location proximal to a closed nose end of the surgical drape;
    passing a lumen attached to the device through an exit port in a first small pocket of the surgical drape extending from the surgical drape near the nose end;
    placing a hand into a second larger pocket behind the first smaller pocket extending into the surgical drape;
    grasping the device with the hand, the surgical drape separating the hand from direct contact with the device; and
    moving the device without direct contact of the hand with the device.

* * * * *